US012632927B2

(12) United States Patent
Park

(10) Patent No.: US 12,632,927 B2
(45) Date of Patent: May 19, 2026

(54) SYSTEM AND METHOD FOR IMPROVED PANORAMIC ULTRASOUND IMAGES

(71) Applicant: GE Precision Healthcare LLC, Waukesha, WI (US)

(72) Inventor: Gwang Hee Park, Yongin-si (KR)

(73) Assignee: GE Precision Healthcare LLC, Waukesha, WI (US)

( * ) Notice: Subject to any disclaimer, the term of this patent is extended or adjusted under 35 U.S.C. 154(b) by 286 days.

(21) Appl. No.: 18/368,265

(22) Filed: Sep. 14, 2023

(65) Prior Publication Data

US 2025/0095107 A1 Mar. 20, 2025

(51) Int. Cl.
| | |
|---|---|
| *G06T 5/50* | (2006.01) |
| *A61B 8/00* | (2006.01) |
| *A61B 8/08* | (2006.01) |
| *G06T 5/00* | (2024.01) |
| *G06T 5/77* | (2024.01) |

(52) U.S. Cl.
CPC .............. *G06T 5/50* (2013.01); *A61B 8/5215* (2013.01); *G06T 5/77* (2024.01); *G06T 2207/10132* (2013.01); *G06T 2207/20081* (2013.01); *G06T 2207/20084* (2013.01)

(58) Field of Classification Search
CPC ... G06T 5/50; G06T 5/77; G06T 2207/10132; G06T 2207/20081; G06T 2207/20084; A61B 8/2515
See application file for complete search history.

(56) References Cited

U.S. PATENT DOCUMENTS

| | | | |
|---|---|---|---|
| 2021/0350539 A1* | 11/2021 | Halmann | ............. A61B 8/5246 |
| 2022/0211352 A1 | 7/2022 | Kim | |
| 2023/0281837 A1* | 9/2023 | De Beni | ................... G06T 7/11 |
| | | | 382/294 |

OTHER PUBLICATIONS

NPL: Results Publication Date Range: Mar. 5, 2019 to Jul. 29, 2025.*
NPL: IP.com and IEEE, Results Publication Date Range: Oct. 31, 2019 to Dec. 24, 2025.*

* cited by examiner

*Primary Examiner* — Quang N Vo
(74) *Attorney, Agent, or Firm* — McAndrews, Held & Malloy, Ltd.; Daniel Bissing; David Bates

(57) ABSTRACT

Systems and methods for acquiring by an ultrasound probe of an ultrasound system, ultrasound image data of an anatomical structure, generating, by at least one processor of the ultrasound system, an acquired panoramic ultrasound image of the anatomical structure based on the ultrasound image data, the acquired panoramic ultrasound image including a loss area, processing, by the at least one processor of the ultrasound system, the acquired panoramic ultrasound image based on one or more reference panoramic ultrasound images without the loss area, and outputting, by the at least one processor of the ultrasound system, an enhanced panoramic ultrasound image without the loss area for presentation on a display system.

20 Claims, 6 Drawing Sheets

400

410

700

702 — Acquire ultrasound image data of a region of interest of an anatomical structure 704 — Produce acquired panoramic ultrasound image 706 — Generate enhanced panoramic ultrasound image

SYSTEM AND METHOD FOR IMPROVED PANORAMIC ULTRASOUND IMAGES

FIELD

Certain embodiments relate to ultrasound imaging. More specifically, certain embodiments relate to a method and system for enhancing panoramic ultrasound images.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Panoramic ultrasound imaging is a powerful tool used to obtain images of organs and soft tissues that are larger than a field of view by stitching images together. The ultrasound probe obtains panoramic ultrasound images by sliding the ultrasound probe across an organ or soft tissue surface and adding image data to the already gathered image data.

However, panoramic ultrasound images may sometimes contain loss area(s) due to a human body's natural curvature. Panoramic ultrasound images may be obtained again in order to attempt to capture a smaller loss area or a diagnosis may be attempted using the panoramic ultrasound image with the loss area.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for enhancing panoramic ultrasound images using deep learning methods, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
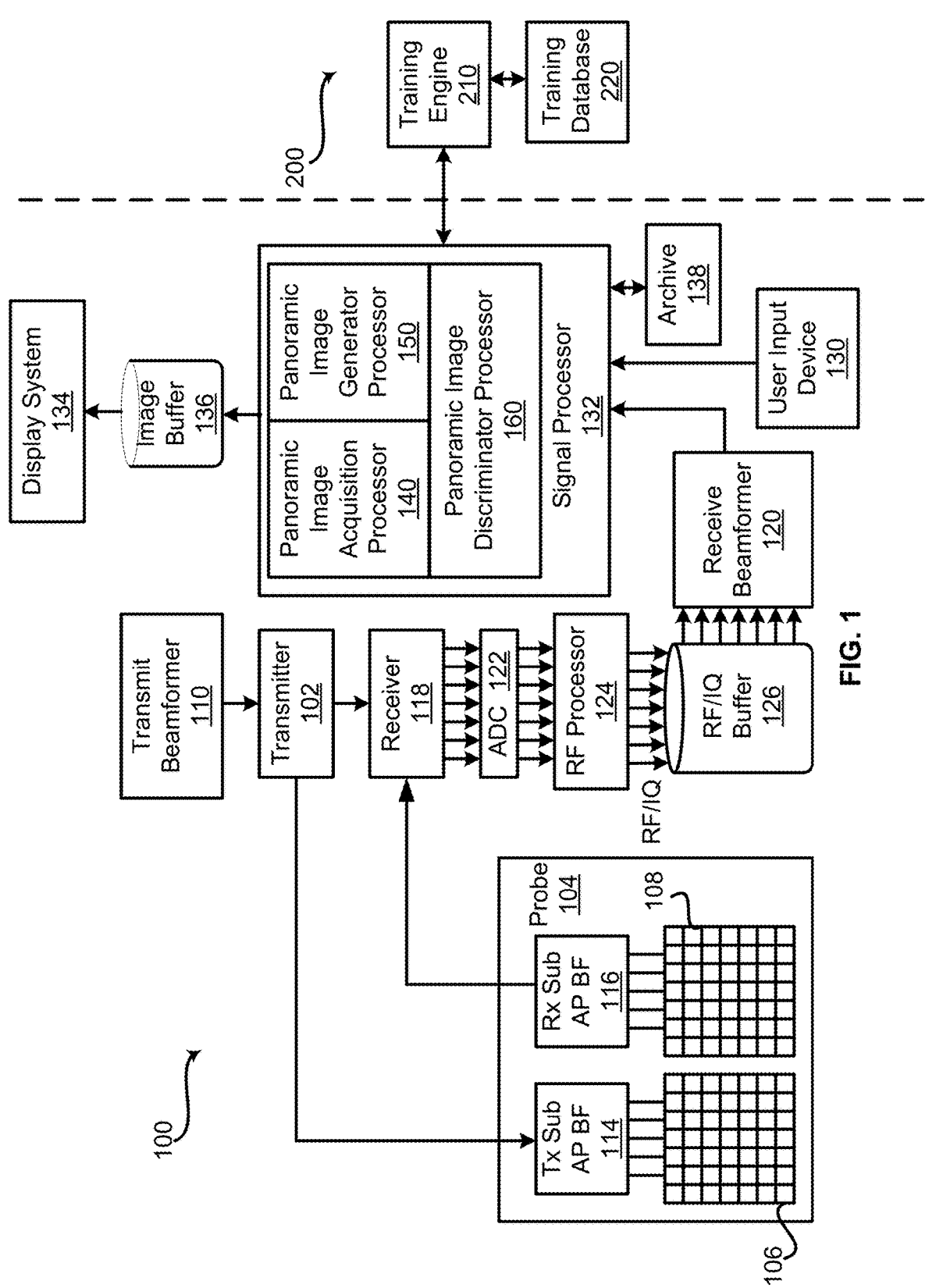
FIG. 1 is a block diagram 100 of an exemplary ultrasound system that is operable for enhancing panoramic ultrasound images using deep learning, in accordance with various embodiments.

Certain embodiments may be found in a method and system for enhancing panoramic ultrasound images using deep learning. Aspects of the present disclosure have the technical effect of enhancing panoramic ultrasound images using deep learning in order to help provide a diagnosis. Various embodiments have the technical effect of processing acquired ultrasound images to enhance panoramic ultrasound images using deep learning. Certain embodiments have the technical effect of processing a degraded panoramic ultrasound image of a region of interest with a loss area with a reference ultrasound image of a same region of interest without a loss area. Aspects of the present disclosure have the technical effect of generating improved ultrasound panoramic images using ultrasound reference images. Various embodiments have the technical effect of processing ultrasound images with a loss area to recover the loss area with a deep learning method, in order to provide a more complete panoramic image to a user to help in diagnosis.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be standalone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical, and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode, which can be one-dimensional (1D), two-dimensional (2D), three-dimensional (3D), or four-dimensional (4D), and comprising Brightness mode (B-mode), Motion mode (M-mode), Color Motion mode (CM-mode), Color Flow mode (CF-mode), Pulsed Wave (PW) Doppler, Continuous Wave (CW) Doppler, Contrast Enhanced Ultrasound (CEUS), and/or sub-modes of B-mode and/or CF-mode such as Harmonic Imaging, Shear Wave Elasticity Imaging (SWEI), Strain Elastography, Tissue Velocity Imaging (TVI), Power Doppler Imaging (PDI), B-flow, Micro Vascular Imaging (MVI), Ultrasound-Guided Attenuation Parameter (UGAP), and the like.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), Digital Signal Processor (DSP), Field-Programmable Gate Array (FPGA), Application-Specific Integrated Circuit (ASIC), or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system that is operable to automatically place a medical device in an anatomical structure using a locking mechanism, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, analog-to-digital (A/D) converters 122, a radio frequency (RF) processor 124, a RF quadrature (RF/IQ) buffer 126, a user input device 130, a signal processor 132, an image buffer 136, a display system 134, and an archive 138.

The transmitter 102 may comprise suitable logic, circuitry, interfaces, and/or code that may be operable to drive an ultrasound probe 104. The ultrasound probe 104 may be a linear, convex, intracavitary, or phased array transducer. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. The group of transmit transducer elements 106 may emit ultrasonic signals through oil and a probe cap and into a target. In a representative embodiment, the ultrasound probe 104 may be operable to acquire ultrasound image data covering at least a substantial portion of an anatomy, such as a heart, an ovary, or any suitable anatomical structure. In an exemplary embodiment, the ultrasound probe 104 may be operated in a volume acquisition mode, where the transducer assembly of the ultrasound probe 104 acquires a plurality of parallel 2D ultrasound slices forming an ultrasound volume.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, and interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces, and/or code that may be operable to demodulate the digital signals output by the plurality of A/D converters 122. In accordance with an embodiment, the RF processor 124 may comprise a complex demodulator (not shown) that is operable to demodulate the digital signals to form me/Q data pairs that are representative of the corresponding echo signals. The RF or I/Q signal data may then be communicated to an RF/IQ buffer 126. The RF/IQ buffer 126 may comprise suitable logic, circuitry, interfaces, and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select target structures for acquisition of images, input and/or select a region of interest, modify a region of interest, select regions of interest used to acquire images, a focused/zoomed volume, and the like. In an exemplary embodiment, the user input device 130 may be operable to configure, manage, and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a panoramic image acquisition processor 140, a panoramic image generator processor 150, and a panoramic image discriminator processor 160. The signal processor 132 may be capable of receiving input information from a user input device 130 and/or archive 138, generating an output displayable by a display system 134, and manipulating the output in response to input information from a user input device 130, among other things. The signal processor 132, a panoramic image acquisition processor 140, and a panoramic image generator processor 150 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a panoramic image acquisition processor 140 that comprises suitable logic, circuitry, interfaces, and/or code that may be operable to use an ultrasound probe 104 to obtain panoramic ultrasound images. In an exemplary embodiment, the panoramic image acquisition processor 140 may be configured to capture panoramic ultrasound images and/or ultrasound image slices to detect and localize a target structure. For example, the panoramic image acquisition processor 140 may be configured to receive a user input selecting a target structure prior to performing an ultrasound image acquisition and analyzing the ultrasound image and/or volume of the ultrasound image acquisition to detect and localize the target structure.

Figure 2:
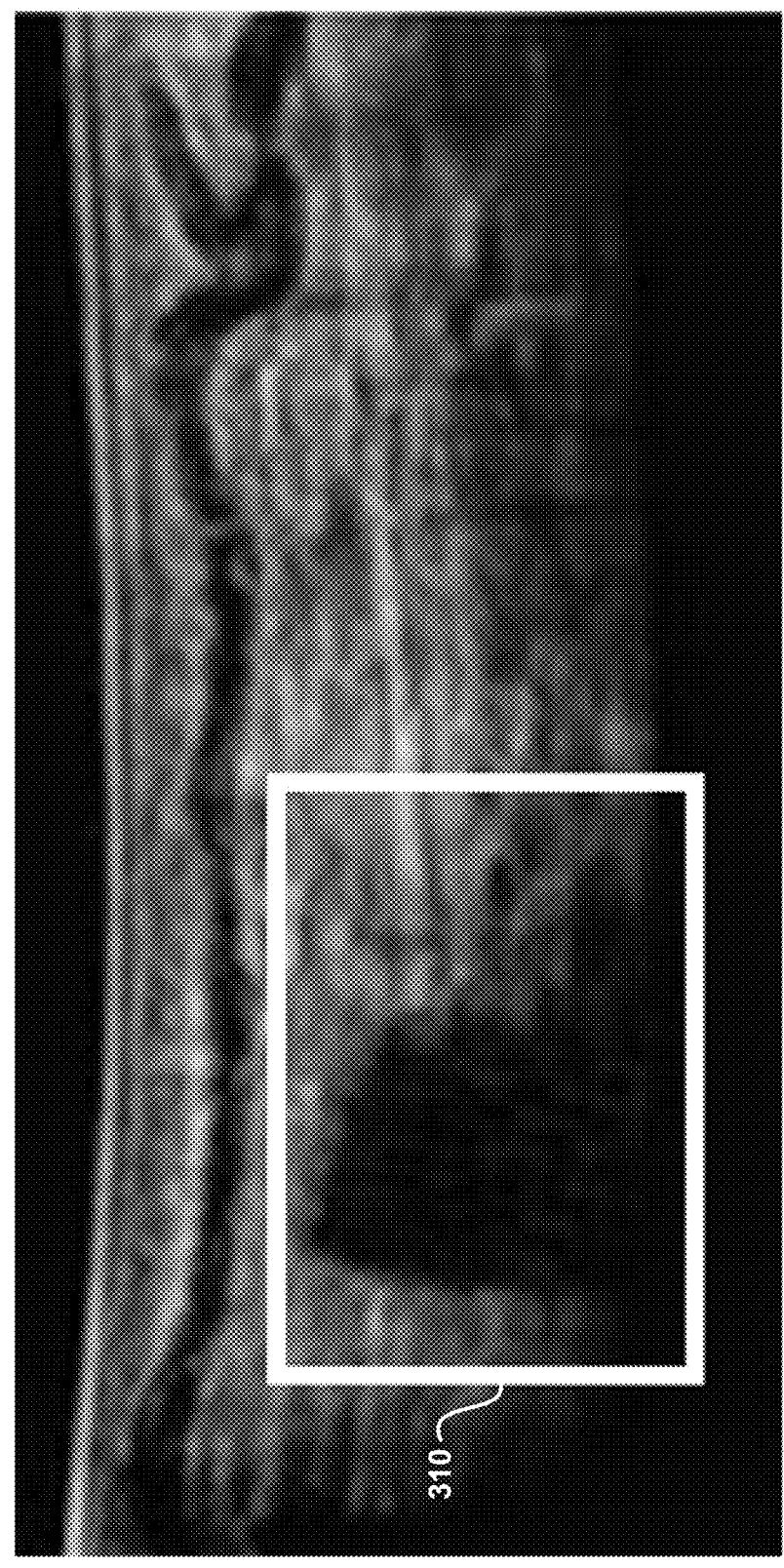
FIG. 2 is an exemplary two-dimensional (2D) panoramic ultrasound image 300 including a loss area, in accordance with various embodiments.

FIG. 2 is an exemplary two-dimensional (2D) panoramic ultrasound image 300 including a loss area 310, in accordance with various embodiments. A user input via a user input device 130 may trigger a panoramic ultrasound image acquisition by the ultrasound probe 104. The ultrasound image acquisition may be a 2D or 3D image acquisition, such as acquiring 2D panoramic ultrasound, 2D biplane, or 3D panoramic ultrasound images by the panoramic image acquisition processor 140. Additionally and/or alternatively, the panoramic ultrasound image acquisition may be a volume acquisition. Additionally and/or alternatively, the detected and localized target structure 312 may be stored at archive 138 and/or any suitable computer readable medium. Additional ultrasound image acquisitions may be acquired automatically and/or in response to a user input. The additional ultrasound image acquisitions may be 2D images, 3D images, or volume acquisitions. For example, the panoramic image acquisition processor 140 may automatically initiate additional ultrasound image acquisition by the ultrasound probe 104 if a user input is not received in a predetermined period of time. As another example, the panoramic image acquisition processor 140 may be configured to initiate additional ultrasound image acquisitions by the ultrasound probe 104 in response to a user input.

Referring again to FIG. 1, the panoramic image acquisition processor 140 may be configured to gather ultrasound image data as the ultrasound probe 104 is glided across a region of interest, an anatomical structure, and/or tissues. As the ultrasound probe 104 is glided across the anatomical structure and/or tissues, the panoramic image acquisition processor 140 gathers ultrasound images and stitches the ultrasound images together to produce panoramic ultrasound images that include the region of interest, anatomical structures, and/or tissues. For example, the panoramic image acquisition processor 140 may produce the acquired panoramic ultrasound image 300. As the ultrasound probe 104 is glided across the region of interest, the stitched ultrasound images may include a loss area 310 for portions of the region of interest where the ultrasound probe is unable to gather ultrasound image data due to natural curvatures of a human anatomy or other tissues.

The acquired panoramic ultrasound image 300 with the loss area 310 may be provided by the panoramic image acquisition processor 140 to the panoramic image generator processor 150. Additionally and/or alternatively, the generated images may be stored at archive 138 and/or any suitable computer readable medium, and the panoramic image generator processor 150 may obtain the panoramic ultrasound images from the archive 138 and/or any suitable computer readable medium. In some examples, the panoramic image acquisition processor 140 may also be used to generate reference panoramic ultrasound images to be stored in an archive 138, training database 220, and/or any suitable computer readable medium.

The signal processor 132 may include a panoramic image generator processor 150 that comprises suitable logic, circuitry, interfaces, and/or code that may be operable to obtain the acquired panoramic ultrasound images 300 from the panoramic image acquisition processor 140 and/or from the archive 138, training database 220, and/or any suitable computer readable medium. For example, the panoramic image generator processor 150 may be configured to receive from the panoramic image acquisition processor 140, or retrieve from the archive 138 and/or training database 220, and/or any suitable data storage medium, the acquired panoramic ultrasound image 300 with the loss area 310.

Figure 3:
FIG. 3 is an exemplary two-dimensional (2D) reference panoramic ultrasound image 400, in accordance with various embodiments

Referring to FIG. 3, FIG. 3 is an exemplary two-dimensional (2D) reference panoramic ultrasound image 400. The reference panoramic ultrasound image 400 may be of the same region of interest, anatomical structure, and/or tissues as panoramic ultrasound image 300. The reference panoramic ultrasound image 400 may be a 2D image, 2D biplane images, 2D biplane image slices extracted from a volume, a rendered volume, and/or any suitable ultrasound image and/or volume rendering (i.e., 2D projection of 3D/4D volume image data). The reference panoramic ultrasound image 400 may be a complete reference ultrasound image without any loss area (e.g., including image data 410 similar to the loss area 310 of panoramic ultrasound image 300). The reference panoramic ultrasound image 400 may be obtained from an archive 138, a training database 220, and/or any suitable data storage medium. The archive 138, training database 220, or other suitable data storage medium may include reference panoramic ultrasound images from a variety of sources and may include a variety of anatomical structures, tissues, and/or regions of interest of structures and/or tissues.

Referring to FIG. 1, the panoramic image generator processor 150 may comprise suitable logic, circuitry, interfaces, and/or code that may be configured to obtain as input a panoramic ultrasound image 300 and learn probability distributions in order to produce sample panoramic ultrasound images. For example, the panoramic image generator processor 150 may obtain a panoramic ultrasound image 300 from the panoramic image acquisition processor 140, an archive 138, and/or any other suitable computer readable medium. The panoramic image generator processor 150 generates sample panoramic ultrasound images that appear to be real (although some sample images are generated and some are real) and are provided to the panoramic image discriminator processor 160. Additionally or alternatively, the sample panoramic ultrasound images may be stored in an archive 138, training database 220, and/or any other suitable computer readable medium, and the panoramic image discriminator processor 160 may retrieve the sample panoramic ultrasound images from the archive 138, training database 220, and/or any other suitable computer readable medium.

Still referring to FIG. 1, the panoramic image discriminator processor 160 may obtain as input, reference panoramic ultrasound images 400 from the panoramic image generator processor 150, a training database 220, an archive 138, and/or any other suitable computer readable medium. The panoramic image discriminator processor 160 may also be configured to obtain sample panoramic ultrasound images from the panoramic image generator processor 150 and use the sample panoramic ultrasound images to learn to distinguish between real images and generated images. The panoramic image generator processor 150 may also be operable to obtain reference panoramic ultrasound images from a training database 220, from an archive 138, and/or from any suitable data storage medium.

Figure 4:
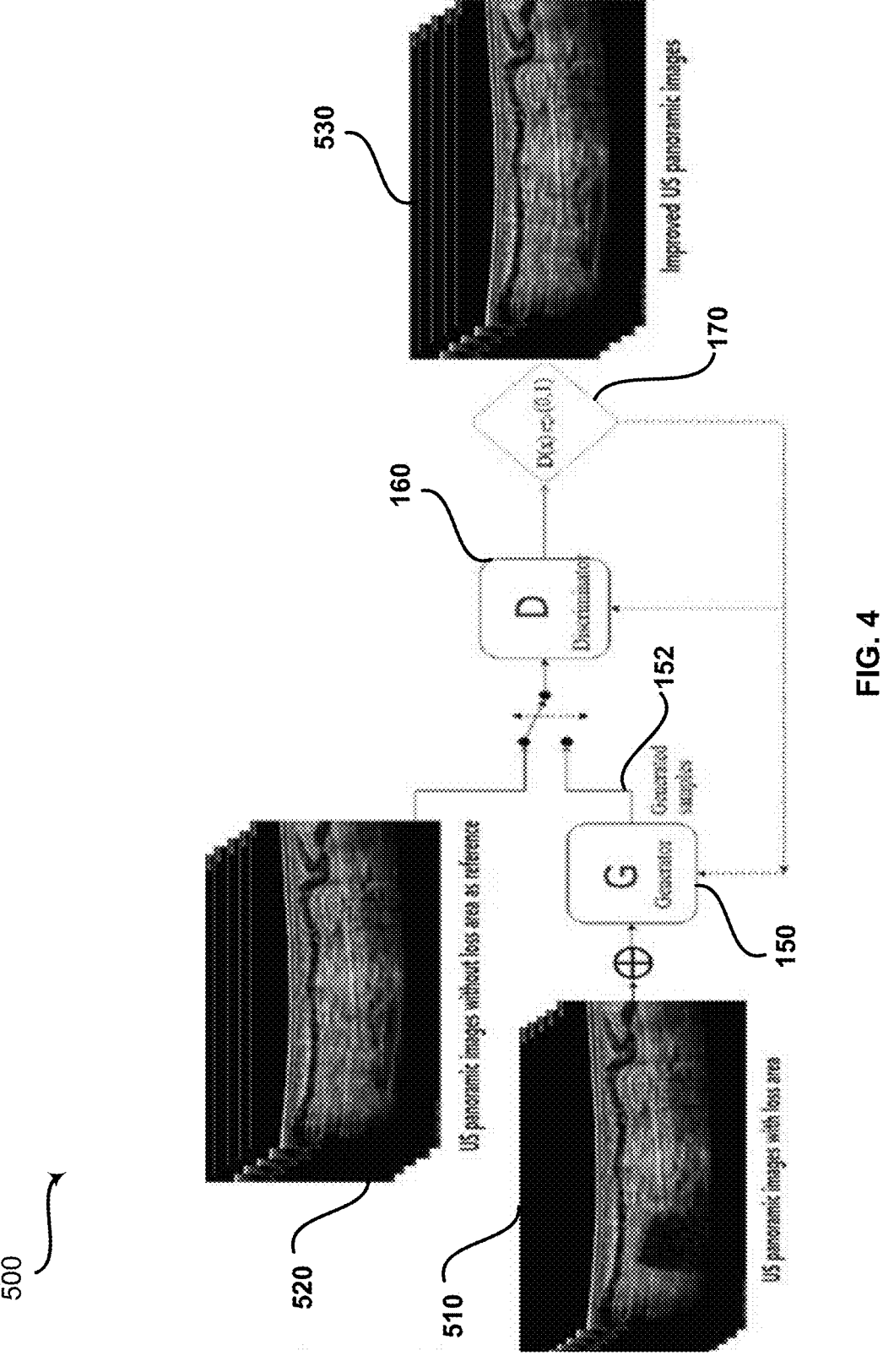
FIG. 4 is an exemplary flow chart 500 of an exemplary deep learning technique, in accordance with various embodiments.

FIG. 4 is a graphical display 500 of an exemplary deep learning technique for improved panoramic ultrasound images, in accordance with various embodiments. Referring to FIG. 4, panoramic ultrasound images with a loss area 510 (e.g., 300 of FIG. 3) are provided as input to the panoramic image generator processor 150. The panoramic image generator processor 150 generates sample panoramic ultrasound images 152 that are provided as input to the panoramic image discriminator processor 160.

In some examples, the deep learning technique is a generative adversarial network (GAN) model, and the panoramic image generator processor 150 and the panoramic image discriminator processor 160 are trained using the GAN model. For example, the panoramic image generator processor 150 may be configured to generate sample panoramic ultrasound images 152 by mapping the panoramic ultrasound images with a loss area 510 to a latent space to learn a probability distribution that the panoramic image generator processor 150 may use to generate sample panoramic ultrasound images 152 that appear to be real. The panoramic image generator 150 may be configured to learn the distribution $p_\theta(x)$, approximate to the real distribution $p_r(x)$ and generate samples $p_G(x)$ that are equal to the probability density function of the real samples $p_r(x)$. For example, the panoramic image generator 150 may learn a differential function $p_\theta(x)$ such that $p_\theta(x) > 0$ and $\int_x p_\theta(x) d(x) = 1$ directly and optimize through maximum likelihood. Additionally or alternatively, the panoramic image generator may learn the differential transformation function $q_\theta(z)$ of $p_\theta(x)$ and optimize through maximum likelihood when z is a distribution such as uniform or Gaussian distribution, as non-limiting examples. The panoramic image generator processor 150 may provide the sample panoramic ultrasound images 152 to the panoramic image discriminator processor 160.

The panoramic image discriminator processor 160 may receive the sample panoramic ultrasound images 152 from the panoramic image generator processor 150 and reference panoramic ultrasound images 520 as inputs and learn to distinguish between real images and generated images. The panoramic image discriminator processor 160 may classify images received as real or generated by outputting a value $D(x)$ 170. In some examples, the value is a binary value (e.g., "0" or "1"). The panoramic image discriminator processor 160 may recognize the data from the real data distribution $p_r(x)$, where D indicates the estimated probability of data points $x_i \in R^n$. In case of binary classification, if the estimated probability $D(x_i) : \rightarrow R^n[0,1]$ is the positive class $p_i$ and $1 - D(x_i) : \rightarrow R[0,1]$ is the negative class $q_i$, the cross entropy distribution between $p_i$ and $q_i$ is $$L(p, q) = \sum_i^n p_i \log q_i.$$

For a given point $x_i$ and corresponding label $y_i$, the data distribution $x_i$ can be from the real data $x_i \sim p_r(x)$ or the generator data $x_i \sim p_g(z)$. The panoramic image generator processor 150 and the panoramic image discriminator processor 160 may have an adversarial relationship in which the panoramic image generator processor 150 produces false generated images and the panoramic image discriminator processor 160 learns to distinguish between real images and generated images. Considering half of the data from the panoramic image generator processor 150 and the panoramic image discriminator processor 160 as real and generated, the panoramic image generator processor 150 and the panoramic image discriminator processor 160 contend with other in order to minimize the loss function.

D(x$_i$) may be provided as feedback to the panoramic image discriminator processor 160 and to the panoramic image generator processor 150. Additionally and/or alternatively, one or more cost and/or loss functions may be used to provide feedback to the panoramic image generator processor 150 and to the panoramic image discriminator processor 160. The loss function may be, for example:

$$\min_{G} \max_{D} L((x_i, y_i)_{i=1}^n, D) =$$

$$-\frac{1}{2}E_{x\sim p_r(x)}\log D(x) - \frac{1}{2}E_{z\sim p_r(z)}\log[1 - D(G(z))] + \lambda\Psi$$

$$\min_{G} \max_{D} L(G, D) = -\frac{1}{2}E_{x\sim p_r(x)}\log D(x) - \frac{1}{2}E_{z\sim p_r(z)}\log[1 - D(G(z))] + \lambda\Psi$$

where $\lambda\Psi = E_{x\sim p_r(x)}[(\|\nabla_x\|^2 - 1)^2]$ is a coefficient to overcome the gradient vanish effect.

By competing and receiving feedback, the panoramic image generator processor 150 may generate images that resemble real ultrasound images, and the panoramic image discriminator processor 160 becomes more adept at distinguishing between real ultrasound images and generated ultrasound images. The objective is for the generated images from the panoramic image generator processor 150 to generate ultrasound images that resemble real ultrasound images, at which point the panoramic image discriminator processor 160 may also be unable to distinguish between real and generated ultrasound images and training may be considered complete.

Once the training of the panoramic image generator processor 150 and the panoramic image discriminator processor 160 using the GAN model is complete, the panoramic image generator processor 150 may generate enhanced panoramic ultrasound images 530. For example, the panoramic image generator processor 150 may obtain an acquired panoramic ultrasound image from the panoramic image acquisition processor 140 and generate an enhanced panoramic ultrasound image 530.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present 2D ultrasound images, 2D panoramic ultrasound images 300, 400, biplane ultrasound images, biplane ultrasound slices extracted from 3D/4D volumes, rendered 3D/4D volumes, selectable target structures, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 2D ultrasound images, 2D panoramic ultrasound images 300, 400, biplane ultrasound images, biplane ultrasound slices extracted from 3D/4D volumes, rendered 3D/4D volumes, instructions for acquiring ultrasound image data, instructions for producing panoramic ultrasound images, instructions for generating sample panoramic ultrasound images, instructions for classifying images as generated or real, instructions for providing feedback based on the classifying of images, instructions for determining that an objective function has been reached, instructions for generating an enhanced panoramic ultrasound image, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 210 may comprise suitable logic, circuitry, interfaces and/or code that may be operable to train the neurons of the deep neural network(s) (e.g., artificial intelligence model(s)) inferenced (i.e., deployed) by the panoramic image acquisition processor 140, the panoramic image generator processor 150, and/or the panoramic image generator processor 160. For example, the artificial intelligence model inferenced by the panoramic image generator processor 150 and/or the panoramic image discriminator processor 160 may be trained to automatically acquire an ultrasound image and/or volume using database(s) 220 of classified ultrasound images and/or volumes of anatomical structures. As another example, the artificial intelligence model inferenced by the panoramic image acquisition processor may be trained to automatically identify target structures, surrounding structures, target structure shapes, major/minor axes of target structures, and the like depicted in an ultrasound volume using database(s) 220 of classified ultrasound volumes of possible target structures.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms. In some examples, the training image databases may include reference panoramic ultrasound images of anatomical structures and/or tissues. In some examples, the reference panoramic ultrasound images may be generated by the panoramic image acquisition processor 140 and provided to the training image databases 220.

Figure 5:
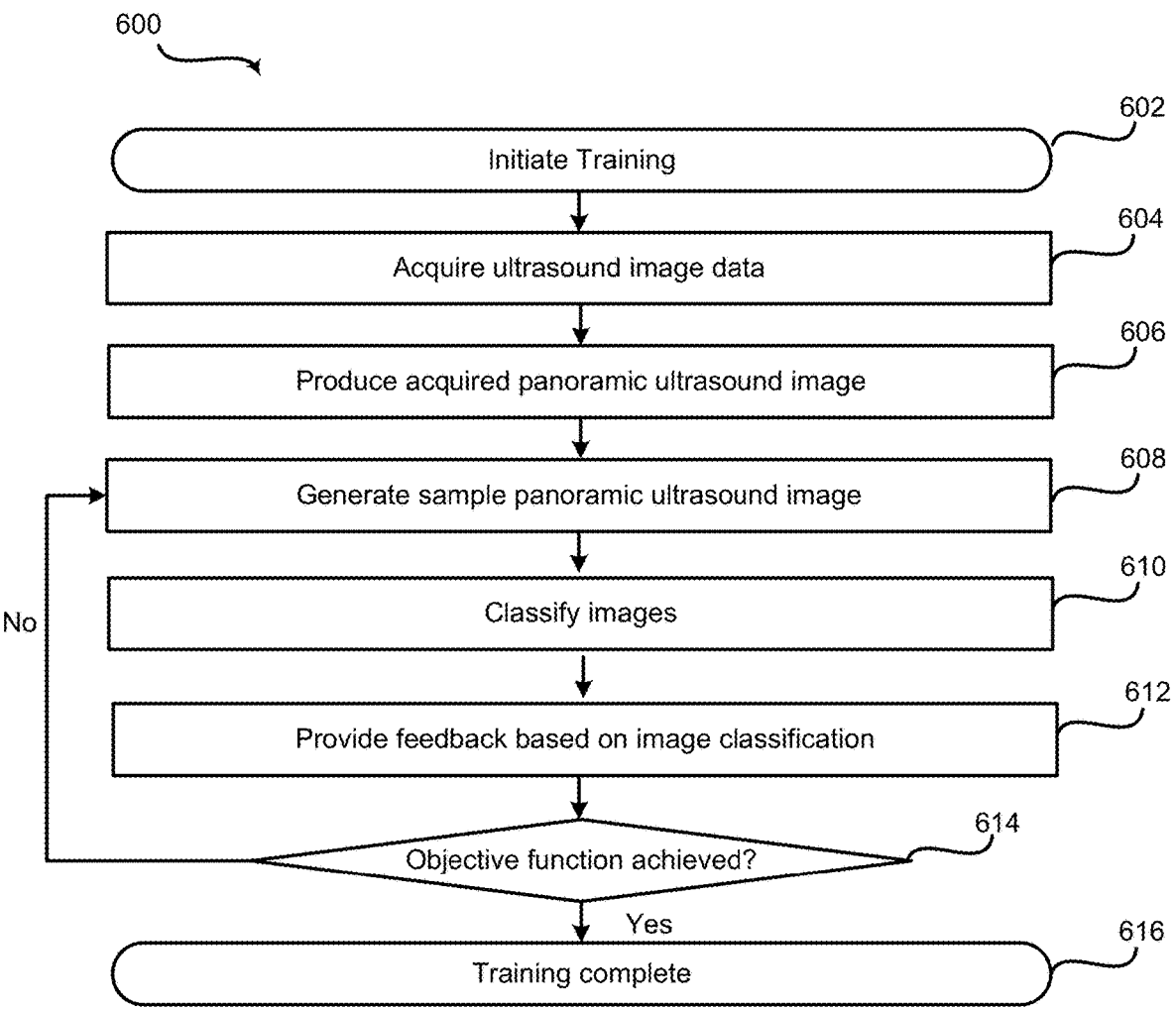
FIG. 5 is a flow chart 600 illustrating exemplary steps that may be utilized for training a deep learning technique for enhancing panoramic ultrasound images, in accordance with various embodiments.

FIG. 5 is a flow chart 600 illustrating exemplary steps 602-616 that may be utilized for training a deep learning technique for enhancing panoramic ultrasound images, in accordance with various embodiments. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 602, a signal processor 132 of the ultrasound system 100 may be configured to initiate training to enhance panoramic ultrasound images. For example, at step 604, a panoramic image acquisition processor 140 may be configured to gather ultrasound image data as the ultrasound probe 104 is glided across a region of interest of an anatomical structure and/or tissues. As the ultrasound probe 104 is glided across the region of interest, the panoramic image acquisition processor 140 gathers ultrasound image data to produce ultrasound images.

At step 606, the signal processor 132 may be configured to produce an acquired panoramic ultrasound image 300. For example, as the ultrasound probe 104 is glided across the region of interest, anatomical structures, and/or tissues, the panoramic image acquisition processor 140 stitches the ultrasound images together to produce acquired panoramic ultrasound images 300. The acquired panoramic ultrasound images 300 may include a loss area 310 for portions of the region of interest, anatomical structure, and/or tissues where the ultrasound probe is unable to gather ultrasound image data due to curvatures of a human anatomy or other tissues. The panoramic image acquisition processor 140 may produce an acquired panoramic ultrasound image 300 and provide the acquired panoramic ultrasound image 300 to the panoramic image generator processor 150.

At step 608, the signal processor 132 may be configured to generate sample panoramic ultrasound image using the acquired panoramic ultrasound image 300. For example, the panoramic ultrasound image generator processor 150 may be configured to map the sample panoramic ultrasound images to a latent space and to learn a probability distribution that the panoramic image generator processor 150 may use to generate sample panoramic ultrasound images. The panoramic image generator processor 150 may provide the sample panoramic ultrasound images to the panoramic image discriminator processor 160.

At step 610, the signal processor 132 may be configured to classify the sample panoramic ultrasound images. For example, the panoramic image discriminator processor 160 may receive the sample panoramic ultrasound images from the panoramic image generator processor 150 and reference panoramic ultrasound images (e.g. 400 of FIG. 4) as input. The panoramic image discriminator processor 160 may classify images received as real or generated.

At step 612, the signal processor 132 may be configured to use the results of the classification in order to provide feedback to the panoramic image generator processor 150 and the panoramic image discriminator processor 160. For example, the panoramic image discriminator processor 160 may classify images received as real or generated by outputting a value D(x). In some examples, the value is a binary value (e.g., "0" or "1"). D(x) may be provided as feedback to the panoramic image discriminator processor 160 and to the panoramic image generator processor 150. Additionally and/or alternatively, one or more cost and/or loss functions may be used to provide feedback to the panoramic image generator processor 150 and to the panoramic image discriminator processor 160.

At step 614, the signal processor 132 may be configured to repeat steps 608-612 until the objective function is achieved. For example, the panoramic image generator processor 150 and the panoramic image discriminator processor 160 may have an adversarial relationship in which the panoramic image generator processor 150 produces false/generated images and the panoramic image discriminator processor 160 learns to distinguish between real panoramic ultrasound images and generated panoramic ultrasound images. By competing and receiving feedback, the panoramic image generator processor 150 may generate panoramic ultrasound images that resemble real panoramic ultrasound images, and the panoramic image discriminator processor 160 becomes more adept at distinguishing between real panoramic ultrasound images and generated panoramic ultrasound images. The objective is for the generated panoramic ultrasound images from the panoramic image generator processor 150 to resemble real ultrasound images, and/or for the panoramic image discriminator processor 160 to be unable to distinguish between real and generated ultrasound images. Once the objective function is achieved, training is complete at step 616.

Figure 6:
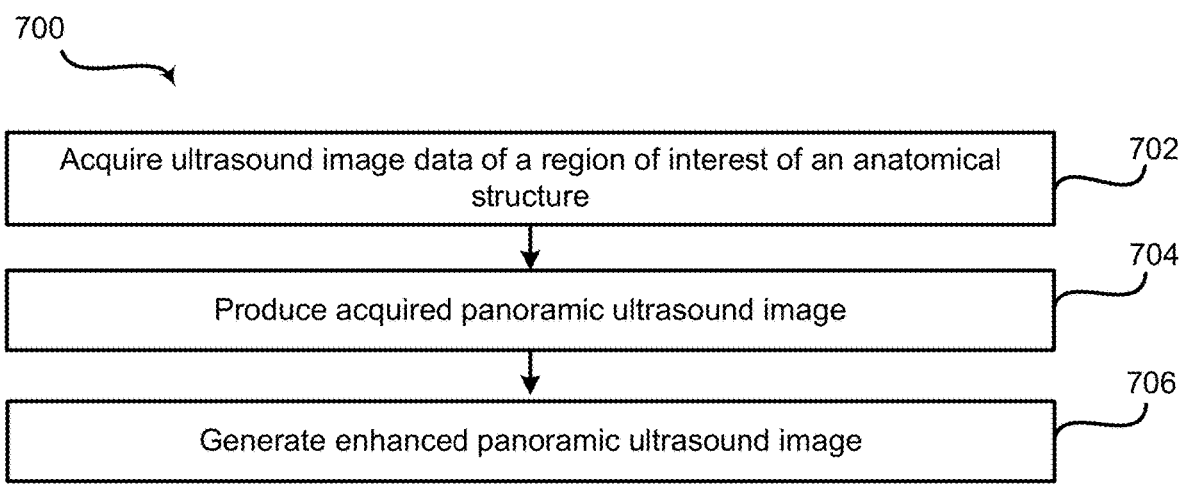
FIG. 6 is a flow chart 700 illustrating exemplary steps that may be utilized for enhancing panoramic ultrasound images using deep learning, in accordance with various embodiments.

FIG. 6 is a flow chart 700 illustrating exemplary steps that may be utilized for enhancing panoramic ultrasound images using deep learning, in accordance with various embodiments. FIG. 6 is a flow chart 700 illustrating exemplary steps 702-706 that may be utilized to enhance panoramic ultrasound images using deep learning, in accordance with various embodiments. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 702, a signal processor 132 of the ultrasound system 100 may be configured to gather ultrasound image data as the ultrasound probe 104 is glided across a region of interest of an anatomical structure and/or tissues. As the ultrasound probe 104 is glided across the region of interest, the panoramic image acquisition processor 140 gathers ultrasound image data and stitches the ultrasound images together to produce acquired panoramic ultrasound images 300.

At step 704, the signal processor 132 may be configured to produce an acquired panoramic ultrasound image 300. For example, as the ultrasound probe is glided across the region of interest, anatomical structures, and/or tissues, the acquired panoramic ultrasound images may include a loss area 310 for portions of the region of interest where the ultrasound probe 104 is unable to gather ultrasound image data due to curvatures of a human anatomy or other tissues. The panoramic image acquisition processor 140 may produce an acquired panoramic ultrasound image 300 and provide the acquired panoramic ultrasound image 300 to the panoramic image generator processor 150.

At step 706, the signal processor 132 may be configured to generate an enhanced panoramic ultrasound image. For example, the panoramic image generator processor 150 that has been trained using, for example the method of FIG. 6, may receive the sample panoramic ultrasound image 300 from the panoramic image acquisition processor 140 and may generate an enhanced panoramic ultrasound image. The enhanced panoramic ultrasound image generated by the panoramic image acquisition processor 140 may be similar to the acquired panoramic ultrasound image, except the enhanced panoramic ultrasound image is complete and does not include a loss area.

Aspects of the present disclosure provide a method 600, 700 and system 100 for enhancing a panoramic ultrasound image. In accordance with various embodiments, the method 600, 700 may comprise acquiring 604, 702 by an ultrasound probe 104 of an ultrasound system 100, ultrasound image data of an anatomical structure, generating 606, 704, by at least one processor 132, 140 of the ultrasound system 100, an acquired panoramic ultrasound image 300 of the anatomical structure based on the ultrasound image data, the acquired panoramic ultrasound image 300 including a loss area 310, 410, processing 608, 706, by the at least one processor 132, 150 of the ultrasound system 100, the acquired panoramic ultrasound image 300 using one or more reference panoramic ultrasound images 400 without the loss area 310, 410, 520; and outputting, by the at least one processor 132, 150 of the ultrasound system 100, an enhanced panoramic ultrasound image without the loss area 310, 410, 530 for presentation on a display system 134. The method 600, 700 may include 2D or 3D ultrasound image data. The method 600, 700 may process the acquired panoramic ultrasound image 300 using a generative adversarial network (GAN) model 152, 170, 602. The GAN model 152, 170, 602 may comprise generating 608, by at least one processor 132, 150 of the ultrasound system 100, one or more sample panoramic ultrasound images 152, 608, obtaining the one or more reference panoramic ultrasound images 400 without the loss area 410, 520, classifying 610, by the at least one processor 132, 160 of the ultrasound system 100, the one or more sample panoramic ultrasound images 152 and the one or more reference panoramic ultrasound images 520, and providing feedback 170, 612 based on the classifying 170, 610 of the one or more sample panoramic ultrasound images 152 and the one or more reference panoramic ultrasound images 400, 520. The feedback 170, 612 may comprise an error rate 170. The feedback 170, 612 comprising an error rate may be a cost function, a loss function, or a probability distribution 170.

The method 600, 700 may comprise learning the loss area 310, 410, of the one or more reference panoramic ultrasound images 400 using deep learning, wherein the learning the loss area 310, 410 is repeated with the one or more reference panoramic ultrasound images until an objective function is reached 614.

Various embodiments provide an ultrasound system 100 comprising an ultrasound probe 104 configured to acquire 604, 702 ultrasound image data of an anatomical structure and at least one processor 132, 140 configured to generate 606, 704 an acquired panoramic ultrasound image 300 of the anatomical structure based on the ultrasound image data, the acquired panoramic ultrasound image 300 including a loss area 310, 410, process 608, 706 the acquired panoramic ultrasound image 300 using one or more reference panoramic ultrasound images 400 without the loss area 310, 410, and output an enhanced panoramic ultrasound image without the loss area 310, 410, 530 for presentation on a display system 134. The ultrasound image data of the ultrasound system 100 may be 2D or 3D. The at least one processor 132, 150 may be further configured to process the acquired panoramic ultrasound image 300 using a generative adversarial network (GAN) model 152, 170, 602. The at least one processor 132, 150 may be further configured to: generate 608 one or more sample panoramic ultrasound images 152, 608, obtain the one or more reference panoramic ultrasound images 400 without the loss area 410, classify 610 the one or more sample panoramic ultrasound images 152, 608 and the one or more reference panoramic ultrasound images 400, 520, and provide feedback 170, 612 based on the classification 170, 610 of the one or more sample panoramic ultrasound images 152, and the one or more reference panoramic ultrasound images 520.

The feedback 170, 612 of the ultrasound system 100 may be a cost function, a loss function, or a probability distribution 170. The feedback 170, 612 may be used to generate additional sample panoramic images 152, 608. The at least one processor 132, 160 may be further configured to learn the loss area 310, 410 of the one or more reference panoramic ultrasound images 400, 520 using deep learning, wherein the learning the loss area 310, 410 is repeated by processing the one or more reference panoramic ultrasound images until an objective function is reached 614.

Various embodiments provide an ultrasound system 100 for enhancing panoramic ultrasound images comprising an ultrasound probe 104 configured to acquire 604, 702 ultrasound image data of an anatomical structure, and at least one processor 132, 140, configured to generate 606, 704 an acquired panoramic ultrasound image 300 of the anatomical structure based on the ultrasound image data, the acquired panoramic ultrasound image 300 including a loss area 310, learn the loss area of using deep learning by processing one or more reference panoramic ultrasound images 400 without the loss area 410, process the acquired panoramic ultrasound image 300 using the learned loss area 410, 520, and output an enhanced panoramic ultrasound image without the loss area 310, 530 for presentation on a display system 134. In some examples, the ultrasound image data is 2D or 3D. The deep learning of the ultrasound system may be performed using a generative adversarial network (GAN) model 152, 170, 602. The at least one processor 132, 150 of the ultrasound system 100 may be further configured to learn the loss area 310, 410 by generating 608 one or more sample panoramic ultrasound images 152, 608, obtaining the one or more reference panoramic ultrasound images 400 without the loss area 410, classifying 610 the one or more sample panoramic ultrasound images 152 and the one or more reference panoramic ultrasound images 400, and provide feedback 170, 612 based on the classification 170, 610 of the one or more sample panoramic ultrasound images 152 and the one or more reference panoramic ultrasound images 400, 520. The feedback 170, 612 of the ultrasound system 100 may be a cost function, a loss function, or a probability distribution 170. The feedback may be used to generate additional sample panoramic images 152, 608.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhancing panoramic ultrasound images using deep learning.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method for enhancing a panoramic ultrasound image comprising:
  acquiring by an ultrasound probe of an ultrasound system, ultrasound image data of an anatomical structure;
  generating, by at least one processor of the ultrasound system, an acquired panoramic ultrasound image of the anatomical structure based on the ultrasound image data, the acquired panoramic ultrasound image including a loss area;
  processing, by the at least one processor of the ultrasound system, the acquired panoramic ultrasound image using one or more reference panoramic ultrasound images without the loss area; and
  outputting, by the at least one processor of the ultrasound system, an enhanced panoramic ultrasound image without the loss area for presentation on a display system.

2. The method of claim 1, wherein the ultrasound image data is 2D or 3D.

3. The method of claim 1, wherein processing the acquired panoramic ultrasound image is performed using a generative adversarial network (GAN) model.

4. The method of claim 3, wherein the GAN model comprises:
  generating, by at least one processor of the ultrasound system, one or more sample panoramic ultrasound images;

obtaining the one or more reference panoramic ultrasound images without the loss area;
  classifying, by the at least one processor of the ultrasound system, the one or more sample panoramic ultrasound images and the one or more reference panoramic ultrasound images; and
  providing feedback based on the classifying of the one or more sample panoramic ultrasound images and the one or more reference panoramic ultrasound images.

5. The method of claim 4, the feedback comprising an error rate.

6. The method of claim 5, wherein the feedback comprising an error rate is a cost function, a loss function, or a probability distribution.

7. The method of claim 1, further comprising learning the loss area of the one or more reference panoramic ultrasound images using deep learning, wherein the learning the loss area is repeated with the one or more reference panoramic ultrasound images until an objective function is reached.

8. An ultrasound system comprising:
  an ultrasound probe configured to:
    acquire ultrasound image data of an anatomical structure; and
  at least one processor configured to:
    generate an acquired panoramic ultrasound image of the anatomical structure based on the ultrasound image data, the acquired panoramic ultrasound image including a loss area;
    process the acquired panoramic ultrasound image using one or more reference panoramic ultrasound images without the loss area; and
    output an enhanced panoramic ultrasound image without the loss area for presentation on a display system.

9. The ultrasound system of claim 8, wherein the ultrasound image data is 2D or 3D.

10. The ultrasound system of claim 8, wherein the at least one processor is further configured to process the acquired panoramic ultrasound image using a generative adversarial network (GAN) model.

11. The ultrasound system of claim 8, wherein the at least one processor is further configured to: generate one or more sample panoramic ultrasound images;
  obtain the one or more reference panoramic ultrasound images without the loss area;
  classify the one or more sample panoramic ultrasound images and the one or more reference panoramic ultrasound images; and
  provide feedback based on the classification of the one or more sample panoramic ultrasound images and the one or more reference panoramic ultrasound images.

12. The ultrasound system of claim 11, wherein the feedback is a cost function, a loss function, or a probability distribution.

13. The ultrasound system of claim 11, wherein the feedback is used to generate additional sample panoramic images.

14. The ultrasound system of claim 8, wherein the at least one processor is further configured to learn the loss area of the one or more reference panoramic ultrasound images using deep learning, wherein the learning the loss area is repeated by processing the one or more reference panoramic ultrasound images until an objective function is reached.

15. An ultrasound system for enhancing panoramic ultrasound images comprising:
  an ultrasound probe configured to:
    acquire ultrasound image data of an anatomical structure; and at least one processor configured to:

generate an acquired panoramic ultrasound image of the anatomical structure based on the ultrasound image data, the acquired panoramic ultrasound image including a loss area;

learn the loss area of using deep learning by processing one or more reference panoramic ultrasound images without the loss area;

process the acquired panoramic ultrasound image using the learned loss area; and output an enhanced panoramic ultrasound image without the loss area for presentation on a display system.

16. The ultrasound system of claim 15, wherein the ultrasound image data is 2D or 3D.

17. The ultrasound system of claim 15, wherein the deep learning is performed using a generative adversarial network (GAN) model.

18. The ultrasound system of claim 15, wherein the at least one processor is further configured to learn the loss area by:

generating one or more sample panoramic ultrasound images;

obtaining the one or more reference panoramic ultrasound images without the loss area;

classifying the one or more sample panoramic ultrasound images and the one or more reference panoramic ultrasound images; and provide feedback based on the classification of the one or more sample panoramic ultrasound images and the one or more reference panoramic ultrasound images.

19. The ultrasound system of claim 18, wherein the feedback is a cost function, a loss function, or a probability distribution.

20. The ultrasound system of claim 18, wherein the feedback is used to generate additional sample panoramic images.

* * * * *